United States Patent
Kral et al.

(10) Patent No.: US 6,412,334 B1
(45) Date of Patent: Jul. 2, 2002

(54) LEAK DETECTOR FOR ENDOSCOPES

(75) Inventors: Jude A. Kral, Twinsburg; Lawrence W. Leasko, Perry; Wynn V. Webb, Streetsboro; Bernard J. Moss, Willowick, all of OH (US)

(73) Assignee: Steris Inc., Temecula, CA (US)

( * ) Notice: Subject to any disclaimer, the term of this patent is extended or adjusted under 35 U.S.C. 154(b) by 0 days.

(21) Appl. No.: 09/498,870

(22) Filed: Feb. 7, 2000

(51) Int. Cl.⁷ .................................................. G01M 3/26
(52) U.S. Cl. ......................................... 73/40; 73/49.2
(58) Field of Search ........................ 73/40, 49.2, 37.9

(56) References Cited

U.S. PATENT DOCUMENTS

| | | | | |
|---|---|---|---|---|
| 4,320,653 A | * | 3/1982 | Bernhardt ....................... 73/40 |
| 4,506,544 A | | 3/1985 | Shimizu |
| 4,527,551 A | * | 7/1985 | Ishii ............................ 600/132 |
| 4,538,593 A | * | 9/1985 | Ishii ............................ 128/4 |
| 4,548,197 A | * | 10/1985 | Kinoshita ................... 600/132 |
| 4,721,123 A | * | 1/1988 | Cosentino et al. ............. 73/37 |
| 4,766,763 A | * | 8/1988 | Kurtz .......................... 73/49.2 |
| 4,896,530 A | * | 1/1990 | Lehmann ..................... 73/49.2 |
| 5,065,350 A | * | 11/1991 | Fedder ........................... 73/40 |
| 5,310,524 A | * | 5/1994 | Campbell et al. ............. 422/33 |
| 5,333,590 A | * | 8/1994 | Thomson ..................... 123/520 |
| 5,494,530 A | * | 2/1996 | Graf ............................... 73/40 |
| 5,508,009 A | * | 4/1996 | Rickloff et al. .............. 422/292 |
| 5,556,607 A | * | 9/1996 | Childers et al. ............. 422/300 |
| 5,578,993 A | * | 11/1996 | Sitabkhan et al. ........... 73/49.2 |
| 5,705,737 A | * | 1/1998 | Liao ........................... 73/49.7 |
| 5,766,744 A | * | 6/1998 | Fanselow et al. ............ 428/213 |
| 5,795,403 A | * | 8/1998 | Biermaier ................. 134/22.12 |
| 5,858,305 A | * | 1/1999 | Malchesky .................... 422/28 |
| 5,882,589 A | * | 3/1999 | Mariotti ........................ 422/98 |
| 5,897,832 A | * | 4/1999 | Porter .......................... 422/28 |
| 6,047,431 A | * | 4/2000 | Canonica ............... 15/104.095 |
| 6,068,815 A | * | 5/2000 | Oberleitner et al. .......... 422/28 |
| 6,076,808 A | * | 6/2000 | Porter .......................... 261/53 |
| 6,089,081 A | * | 7/2000 | Cook et al. .................... 73/40 |
| 6,279,383 B1 | * | 8/2001 | Balke et al. ................... 73/40 |

FOREIGN PATENT DOCUMENTS

| | | | | |
|---|---|---|---|---|
| GB | 2078380 | * | 1/1982 | |
| JP | 03243843 | * | 10/1991 | ............. 73/49.2 |
| JP | 04102431 | * | 4/1992 | |

* cited by examiner

Primary Examiner—Hezron Williams
Assistant Examiner—Michael Cygan
(74) Attorney, Agent, or Firm—Fay, Sharpe, Fagan, Minnich & McKee, LLP (57) ABSTRACT

In automated reprocessing system (B), a leak detection system (10) evaluates the integrity of a device, such as an endoscope (A), having an internal passage (66). The leak detection system includes an interior chamber (42) which is connected to the internal passage by quick connects (18, 20). A source of compressed air (22) supplies the chamber and internal passage with air to a suitable test pressure. A pressure sensor (50) and a temperature sensor (54), in communication with the chamber, detect the pressure and temperature within the chamber and hence in the endoscope passage. Pressure and temperature measurements made over time are used to determine changes in the gas volume, indicative of whether leaks are present in the endoscope. If the endoscope is determined to be free of leaks, the endoscope is washed and microbially decontaminated in the reprocessing system.

16 Claims, 8 Drawing Sheets

LEAK DETECTOR FOR ENDOSCOPES

BACKGROUND OF THE INVENTION

The present invention relates to a leak detector for lumened instruments. It finds particular application as a leak detector for endoscopes of the watertight type. It will be appreciated, however, that the invention is also applicable to the detection of leaks in other lumened devices.

Endoscopes and other lumened medical instruments are typically subjected to a thorough cleaning and antimicrobial decontamination between each use. During endoscopic procedures, the devices become coated with blood and other protein-rich body fluids. The endoscopes have a watertight structure in which elements that are sensitive to water, detergents, and antimicrobial agents are contained so that it is possible to wash and sterilize the whole body of the endoscope by immersion or spraying in a washing liquid and an antiseptic solution. However, when there are defects in the watertight structure of the sensitive elements, or pinholes and cracks in a sheath of the endoscope's flexible tube, washing and antiseptic solutions can leak into the inside of the water tight portions of the endoscope. This may lead to corrosion of the operating devices, or leakage of the solutions into the bundle of optical fibers, resulting in hindrance of transmission of light. In addition, patients could be harmed if trapped washing or antiseptic liquids later leak from the inside of the endoscope while in use.

To minimize these problems, methods have been developed to detect for leaks in an endoscope. In a conventional leak test procedure, a source of compressed air is attached to the endoscope. The source exhaust port is closed and the endoscope pressurized until a pressure gauge registers that the pressure within it is within a predetermined "pressure hold" range (typically 1140 to 220 mm of mercury). An observation is made to verify that the scope holds this pressure without falling outside the range. Falling outside this range would indicate a gross leak. The endoscope is then totally submerged in a tub of warm water. If the pressure drops, the endoscope is considered leaky and the test discontinued. If the pressure is maintained in the pressure hold range, the operator is instructed to articulate the control handle knobs of the endoscope to flex the distal tip of the endoscope, and visually inspect the device for bubble generation. An inability to maintain pressure during the pressure hold phase, or the generation of a single bubble in a period of one to two minutes is considered to be an endoscope failure. The operator is instructed to discontinue endoscope reprocessing until the device has been inspected and repaired.

The manual leak check procedure is prone to human error, especially with the increasing demand for rapid reprocessing and turnaround of endoscope devices. For example, bubbles may not become evident until two to three minutes into the pressure hold phase. This is well beyond the one to two minutes time frame allotted for the typical leak check. Another problem with the manual leak check procedure is the potential for the operator to leave the endoscope pressurized during subsequent reprocessing. If this occurs, the distal tip will inflate, as the internal pressure increases in the elevated temperature of the processing solution (typically about 50° C.). This can lead to extensive endoscope damage and costly repairs.

Some automated reprocessing systems include a leak check step prior to disinfection of the endoscope. However, changes in ambient temperature can lead to increases in the internal pressure within the endoscope and lead to erroneous assessments. The reprocessing vessel is frequently warm from a prior reprocessing procedure and the internal temperature of the endoscope often rises, as a result, during the leak check.

The present invention provides a new and improved leak detector and method of use, which overcomes the above-referenced problems and others.

SUMMARY OF THE INVENTION

In accordance with one aspect of the present invention, a leak detection system for evaluating the integrity of a device with an internal passage is provided. The system includes an interior chamber. A connector is adapted for releasably connecting the interior chamber with the internal passage of the device. A source of a compressed gas is fluidly connected with the interior chamber and supplies the interior chamber and the internal passage with gas. A pressure sensor and a temperature sensor in communication with the interior chamber detect pressure and temperature within the interior chamber. A valve selectively seals the interior chamber and the internal passage from the source of compressed gas.

In accordance with another aspect of the present invention, a method for detecting the integrity of a device with an internal passage is provided. The method includes supplying a quantity of gas under pressure to the internal passage of the device and measuring a temperature and a pressure of the gas within the internal passage at a first time. The method further includes holding the quantity of gas within the internal passage and measuring the temperature of the gas within the internal passage at a second time. The method further includes determining a function of the temperature and the pressure of the gas within the internal passage at the first and second times, the function indicating whether leakage of the gas from the internal passage has occurred.

In accordance with another aspect of the present invention, a system for reprocessing a device with an internal passage is provided. The system includes a vessel for receiving the device and a source of a liquid microbial decontaminant connected with the chamber, which supplies the decontaminant to the chamber for microbially decontaminating the device. A leak detection system is provided for evaluating the integrity of the internal passage. The leak detection system includes a source of compressed gas selectively connectable with the internal passage, which supplies the internal passage with gas, a pressure sensor and a temperature sensor, in communication with the internal passage, which detect pressure and temperature within the internal passage, and a valve, which selectively seals the internal passage from the source of compressed gas.

In accordance with another aspect of the present invention, a method of reprocessing endoscopes is provided. The method includes positioning an endoscope in a vessel, connecting a leak detector to the endoscope, and supplying a quantity of compressed gas to an internal passage of the endoscope to pressurize the internal passage. The method further includes determining whether the endoscope has leaks from changes in the temperature and pressure of the gas with time, and in the event that the endoscope is determined not to have leaks, supplying a decontamination solution to the vessel to contact and decontaminate the endoscope.

One advantage of the present invention resides in rapid detection of leaks in an endoscope. Another advantage of the present invention resides in its compensation for variations in ambient temperature.

Yet another advantage of the present invention is that it minimizes the potential for operator errors.

Still further advantages and benefits of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENTS

Figure 1:
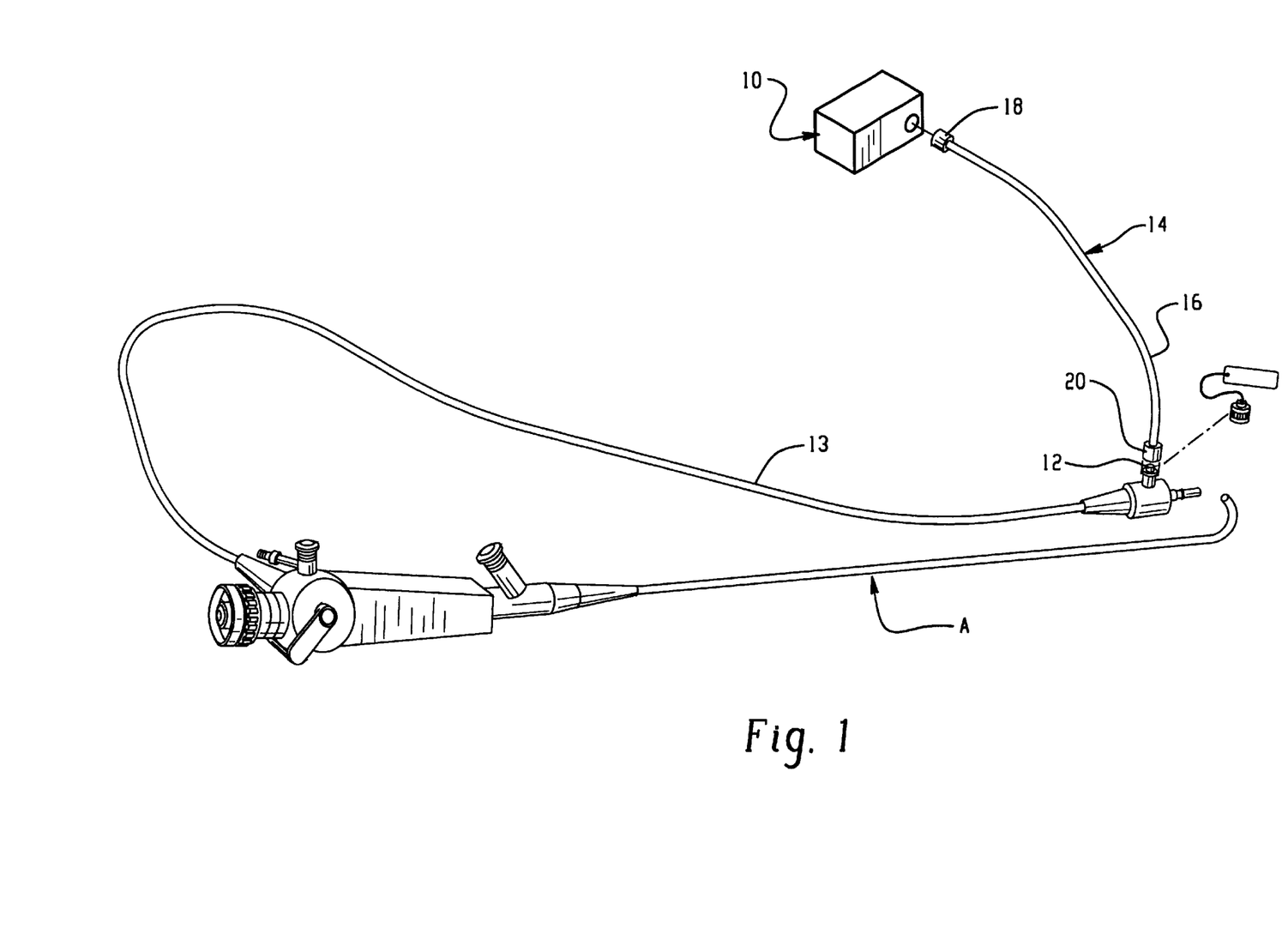
FIG. 1 is a perspective view of a leak detector connected to an endoscope according to the present invention.
Figure 2:
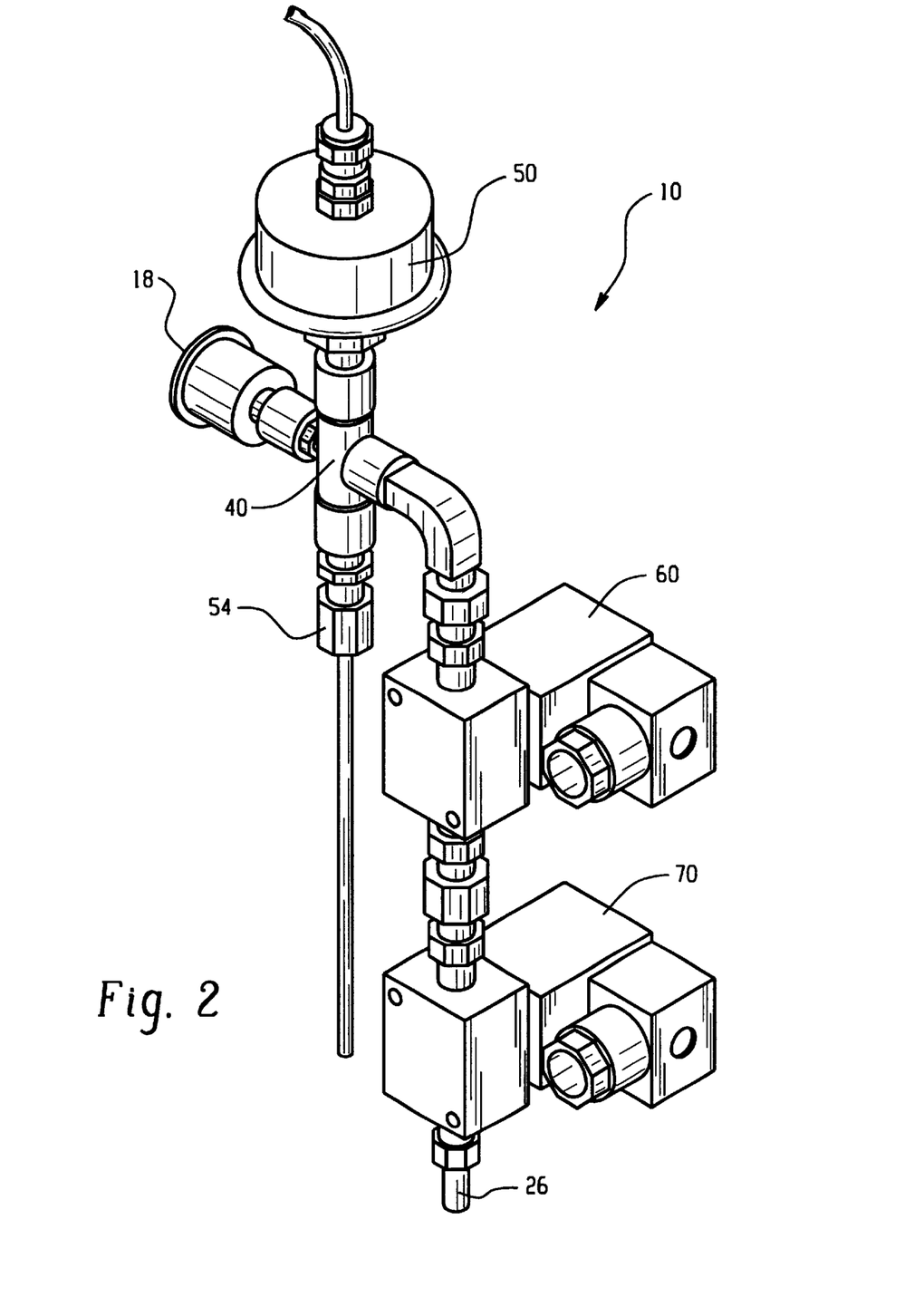
FIG. 2 is a perspective view of the leak detector of FIG. 1.
Figure 3:
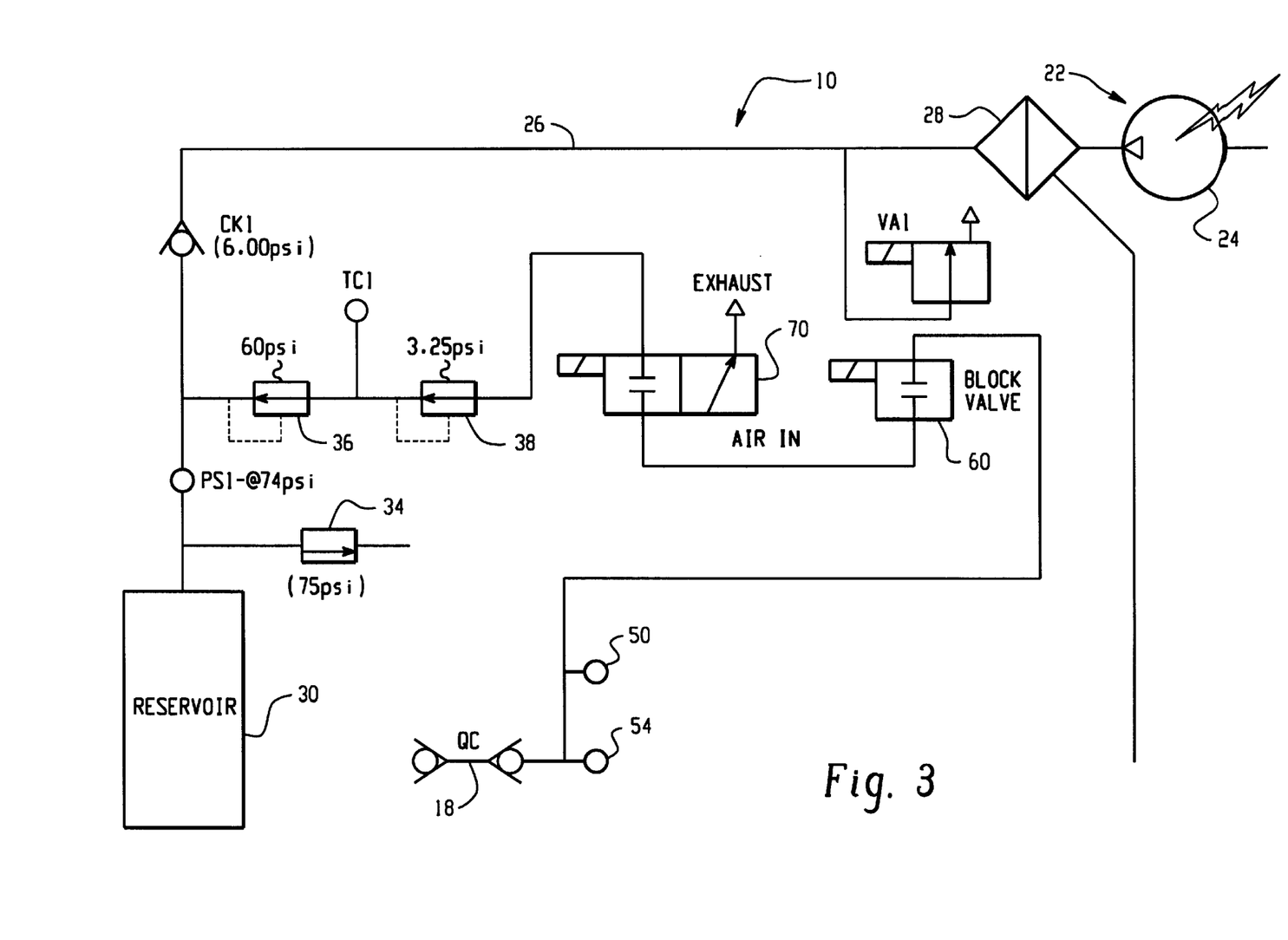
FIG. 3 is a schematic diagram of the leak detector of FIG. 2.

With reference to FIG. 1, a leak detector 10 detects for leaks in an endoscope A or other lumened device. The leak detector is coupled with a leak test port 12 of an endoscope umbilical cable 13, or other entry port be tested, by a removable connector 14. The connector includes a tubular portion 16, with quick connecting members 18, 20 at opposite ends of the connector. The members 18, 20 are adapted for quickly connecting and disconnecting the connector with the leak detector and the inlet port, respectively, providing a leak tight connection therebetween. The tubing 16 is formed from a material which is relatively rigid and does not tend to stretch when under pressures of about 150–300 mmHg.

With reference now to FIGS. 1 to 4, a source of a compressed gas 22, such as an air compressor or cylinder of pressurized gas 24, supplies compressed air to the leak detector 10 via a fluid line 26. The air is passed through a filter 28 to remove airborne particles. Preferably, the filter 28 (or another desiccating device) also removes moisture from the air.

Optionally, the source of compressed gas also includes a reservoir 30, which is filled from the air compressor prior to a leak test procedure. The leak detector includes one or more pressure regulators 34, 36, 38, which reduce the pressure of the air from the source of compressed gas to a suitable pressure for evaluating the endoscope, typically about 140–190 mmHg. The pressure should be below the maximum rating of the endoscope lumen to be tested but sufficiently high that leaks are apparent during the period of detection.

Figure 4:
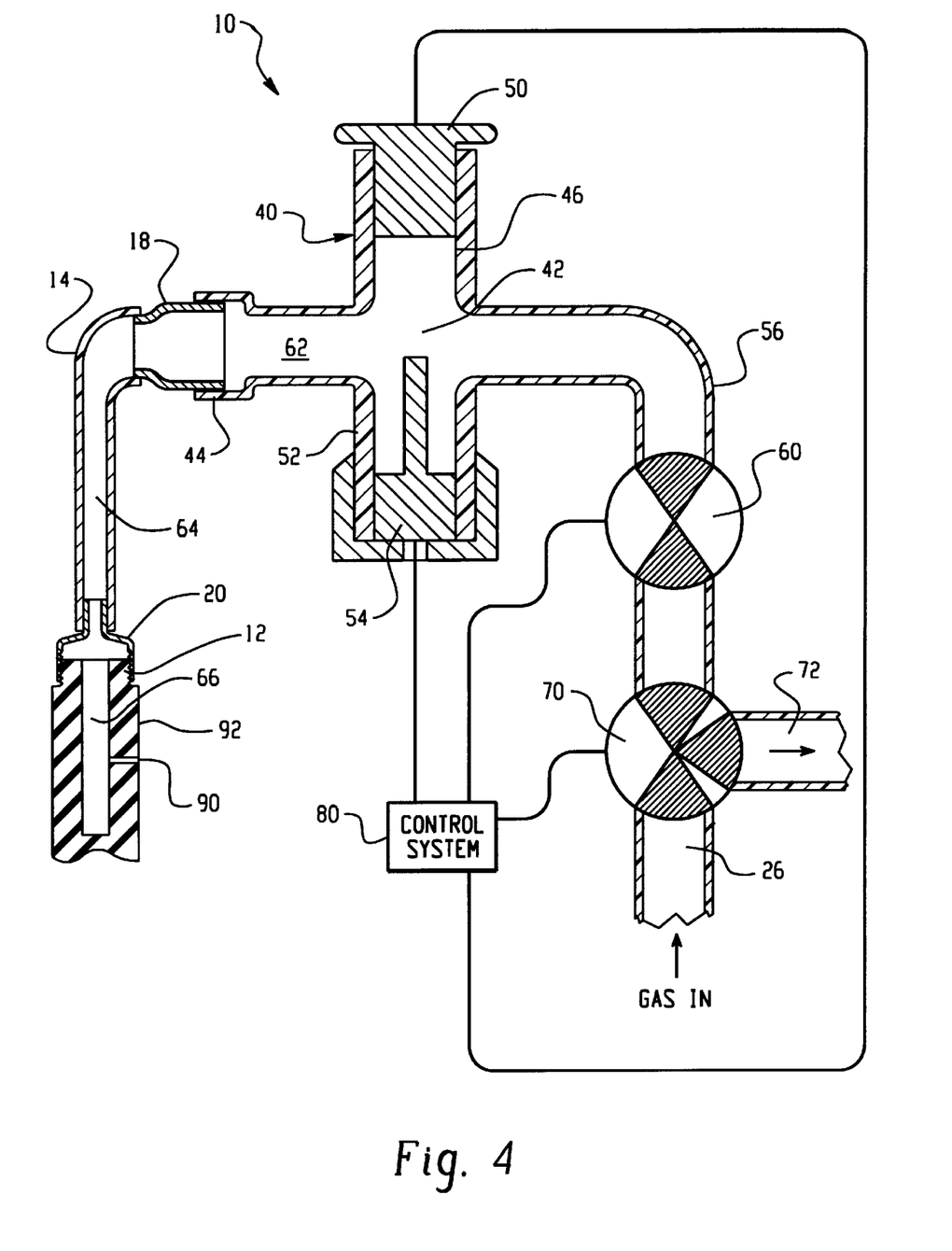
FIG. 4 is a side sectional view of the leak detector of FIG. 2.

With particular reference to FIG. 4, the leak detector 10 includes a cross-shaped tubular member 40 which defines an interior chamber 42 with four connection ports. A first of the connection ports 44 is adapted for connection with the connector quick connect 18. A second inlet port 46 receives a pressure transducer 50, which measures the pressure of the gas within the chamber 42, and, hence, also the pressure within the internal passage of the endoscope. A third inlet port 52 is connected to a temperature detector 54, such as a resistive temperature device, which measures the temperature of the gas within the chamber, and hence also the temperature within the internal passage of the endoscope. A fourth inlet port 56 is connected with the fluid line 26.

A two-way solenoid valve 60 selectively closes the fluid line 26 to seal the fourth inlet port 56. An enclosed space 62 of volume $V_1$, is thus defined, which includes the chamber 42, an internal passage 64 of the connector 14, and the lumen 66 of the endoscope to be evaluated.

A three-way solenoid valve 70 is preferably provided between the two-way solenoid valve 60 and the source 22 of compressed air to allow venting of the space 62, through a vent line 72 before and after leak testing, and to reduce back-pressure on the two-way solenoid valve during leak testing. While the system is described with reference to solenoid valves, other valves may be used. The valves preferably provide a high degree of leak resistance and open and close under automated control accurately and reproducibly.

A control system 80 receives pressure signals from the pressure transducer 50 and temperature signals from the temperature detector 54, and controls the opening and closing of the valves 60 and 70.

To test for leaks, the enclosed space 62 is filled with gas to a set pressure $P_0$. If there are no leaks in the endoscope A, the pressure of gas in the enclosed space, should remain constant over time. However, because the temperature of the gas tends to change over the detection period, the pressure of the gas also tends to change, irrespective of any leaks. Thus, preferably, pressure alone is not used for determining leaks. Accordingly, both temperature and pressure are used to determine whether leakage is occurring. The Ideal Gas Law (1) is used to calculate changes in gas volume during a detection period:

$$V_\theta = \frac{nRT}{P} / P, \qquad (1)$$

where

V=volume n=number of moles of gas

R=universal gas constant

T=absolute temperature (in degrees K)

P=pressure

The number of moles n admitted to the enclosed space 62 can be determined from the time taken to reach an initial pressure $P_0$. Then, an initial volume $V_0$ can be calculated from Equation (1).

If there are leaks in the endoscope's internal passage 66, such as pinholes 90 extending through the outer sheath 92 of the endoscope, then the effective volume V of the gas increases. By measuring temperature and pressure at time $t_1$ and a later time $t_2$, such changes in gas volume can be determined using Boyle's Law, Equation (2):

$$\frac{P_1 V_1}{T_1} = \frac{P_2 V_2}{T_2}, \qquad (2)$$

where $P_1$, $V_1$, and $T_1$, are the pressure, volume, and temperature of the gas at time $t_1$ and $P_2$, $V_2$ and $T_2$ are the pressure, volume, and temperature at time $T_2$.

It will be appreciated that the volumes V determined using this equation are not necessarily absolute volumes. Specifically, the leakage of gas from the endoscope which results in a pressure drop, will lead to an increase in calculated volume V (at constant T).

If the change in volume $(V_2-V_1)$ is above a preselected level, or if the ratio of $V_2/V_1$ is above a preselected value (which avoids the need to determine an initial value of $V_1$), the endoscope is considered to be defective and is examined and repaired prior to further leak testing.

Alternatively, a rate of change in volume is determined:

$$\frac{V_2 - V_1}{t_2 - t_1}. \qquad (3)$$

If the rate of change in volume is more than a preselected level (such as greater than 1 cc/minute), the endoscope is considered to be defective.

Figure 5:
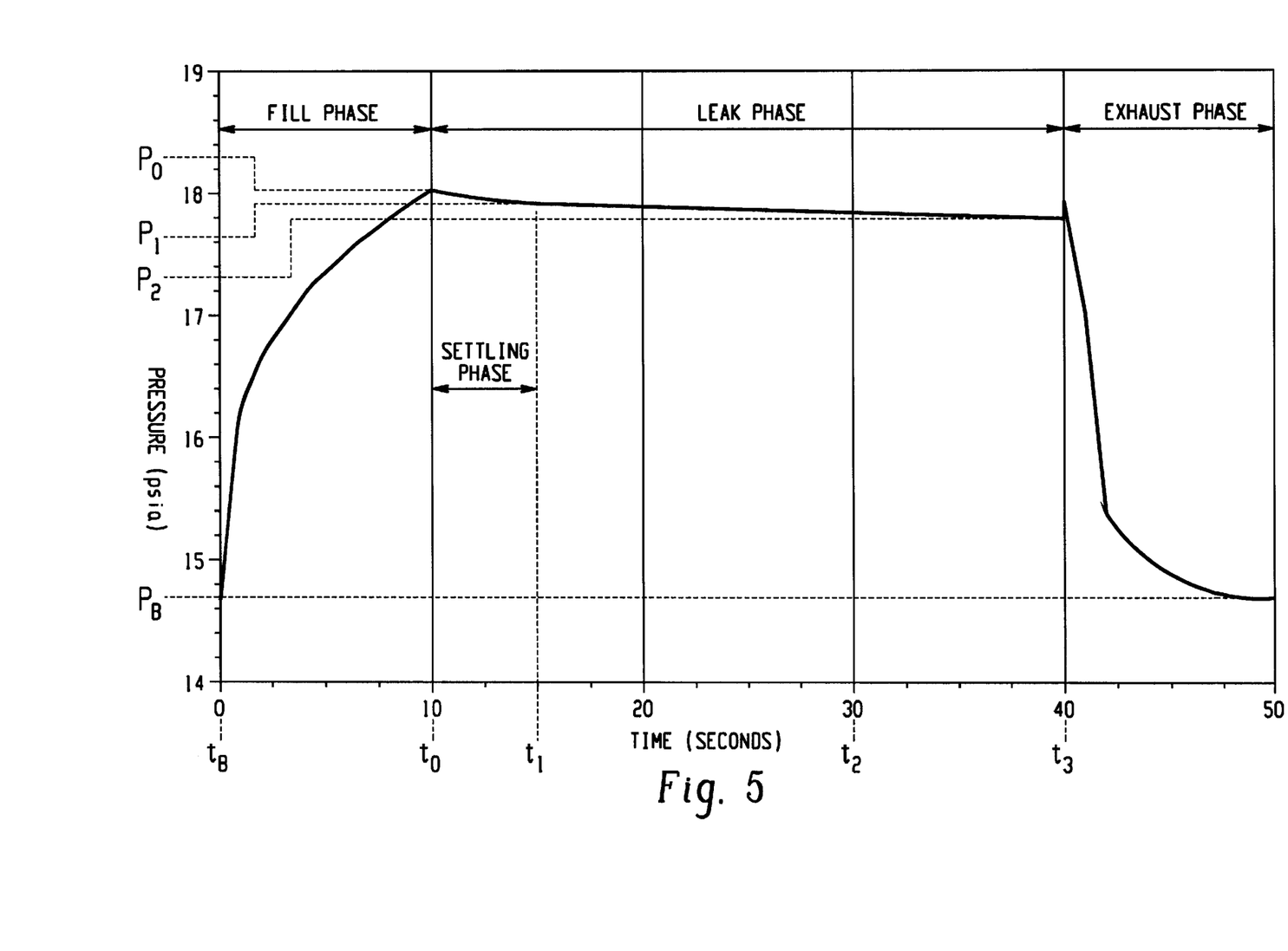
FIG. 5 is a plot of pressure vs time during a leak detection procedure.
Figure 6A:
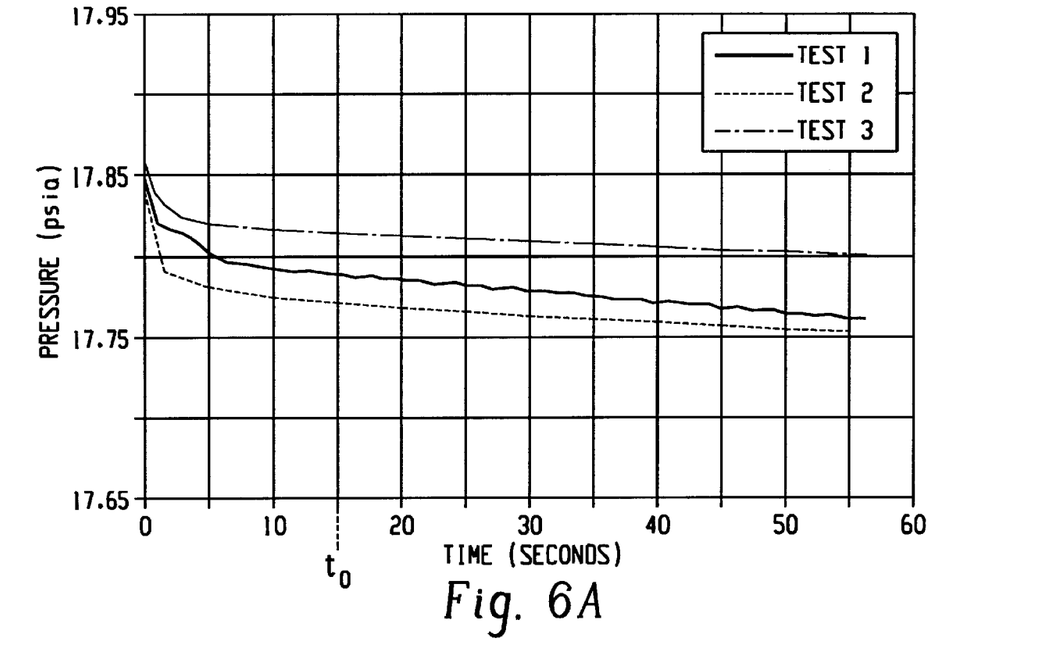
FIG. 6A is a plot of pressure vs time and FIG. 6B is a plot of rate of change in volume vs time for a satisfactory endoscope.
Figure 6B:
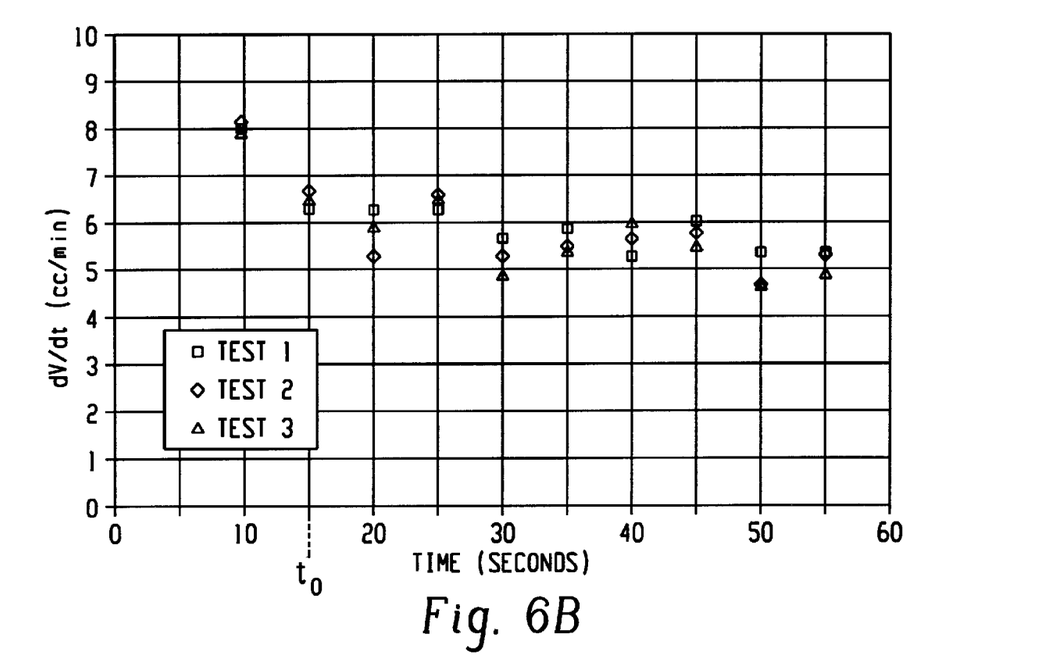

With reference to FIG. 5, the rate of change in volume is preferably calculated for two time periods, namely a first period from $t_1$ to $t_2$, and a second, subsequent period from $t_2$ to $t_3$. If the rate of change is decreasing, this indicates that the endoscope volume may have undergone initial expansion due to stretching of flexible portions under the pressure used.

To perform a leak test, the leak detector 10 is connected with the leak test port of the endoscope A. The control system 80 signals the two way solenoid valve 60 to open, and signals the three-way valve 70 to connect the two-way valve with the vent line 72, thereby venting the enclosed space 62 to the atmosphere.

After a short rest period (about 0.35 seconds), the control system 80 closes the 2-way valve and the baseline values of pressure $P_B$ and temperature $T_B$ are detected by the pressure transducer 50 and temperature detector 54 at time $t_B$.

The 2-way solenoid valve 60 and the 3-way solenoid valve 70 are then both energized by the control system, allowing the endoscope lumen to fill to a preselected destination pressure $P_0$ (the Fill phase). The preselected destination pressure is preferably about 175–190 mmHg psi above the baseline pressure $P_B$. If the destination pressure is not reached within a preselected time period, such as 15 seconds, the leak detection cycle is aborted. The failure of the endoscope to reach the destination pressure indicates that either the endoscope A is significantly damaged as it will not hold pressure, or that leak-tight connections between the endoscope and the leak detector 10 have not been properly made. The connections are checked and, if necessary, the damaged endoscope is sent for inspection and repair prior to retesting. once the destination pressure $P_0$ is met, the 2-way valve 60 is unpowered to close the valve, sealing the enclosed space 62 at the destination pressure. The time taken to reach the destination pressure ($t_0 - t_B$) is recorded and can be used to determine the initial volume $V_0$ of gas in the enclosed space 62.

The three way valve 70 is then de-energized to vent pressure between the 2-way and 3-way valves to line 72 to prevent valve seal fluctuation. The pressure and temperature of the air within the endoscope passage are allowed to equilibrate for a settling phase, from $t_0$ to $t_1$, preferably about 5 seconds. At the end of the settling phase, the pressure $P_1$ and temperature T are again recorded and can be used to determine $V_1$. If during the settling phase, the endoscope pressure drops to below about 150 mmHg, the cycle is aborted and the endoscope is failed. The settling phase is used to allow for any stretching of the endoscope due to the pressures applied.

A read phase begins at $t_1$, during which time pressure and temperature readings are made at intervals. For example, after a further 15 seconds ($t_2$), readings of temperature $t_2$ and pressure $P_2$ are made. The process is repeated after a further 15 seconds, at time $t_3$. The pressure and temperature readings are used to calculate the effective volumes $V_2$ and $V_3$ of gas corresponding to the temperature and pressure readings at $t_2$ and $t_3$. Using the measurements of volume over time, the control system 80 uses an algorithm to calculate a rate of change in the volume, or other function of pressure and temperature which is indicative of whether there is a leakage of the gas from the enclosed space. If the function measured is outside a preselected range, the control system 80 indicates that further processing is not to be undertaken until the endoscope is examined for damage. For example, if the rate of volume change is in excess of about 1 cc/minute, the endoscope is determined to be defective and is subjected to examination and repair, as appropriate.

Once of the integrity of the endoscope A has been determined, the control system 80 signals the 2-way solenoid valve 60 to open and the three-way solenoid valve 70 to vent to the ambient through vent line 72, removing all pressure from the endoscope sheath (the Exhaust phase).

With reference to FIGS. 6A, 6B, 7A, and 7B, representative plots of pressure versus time and rate of change in volume with time (dv/dt) are shown for two endoscopes tested for leaks using the apparatus of FIGS. 1–4. For improved evaluation of the system, measurements of pressure and temperature were made at 5 second intervals, although, as discussed above, fewer measurements may be made in a leak test check. For each endoscope, the test was repeated three times to assess reproducibility.

The results show good reproducibility of the system. The endoscope of FIGS. 6A and 6B passed the leak detection test. During the read phase from $t_{30}$ to $t_{45}$, the rate of change of volume did not exceed about 1.0 cc/min and the average volume change was less than 1 cc/minute. Moreover, the rate of change of volume approached zero asymptotically over time, suggesting that the endoscope may have undergone some initial stretching in the first few seconds of the test, but was not exhibiting significant change in volume due to leaks.

Figure 7A:
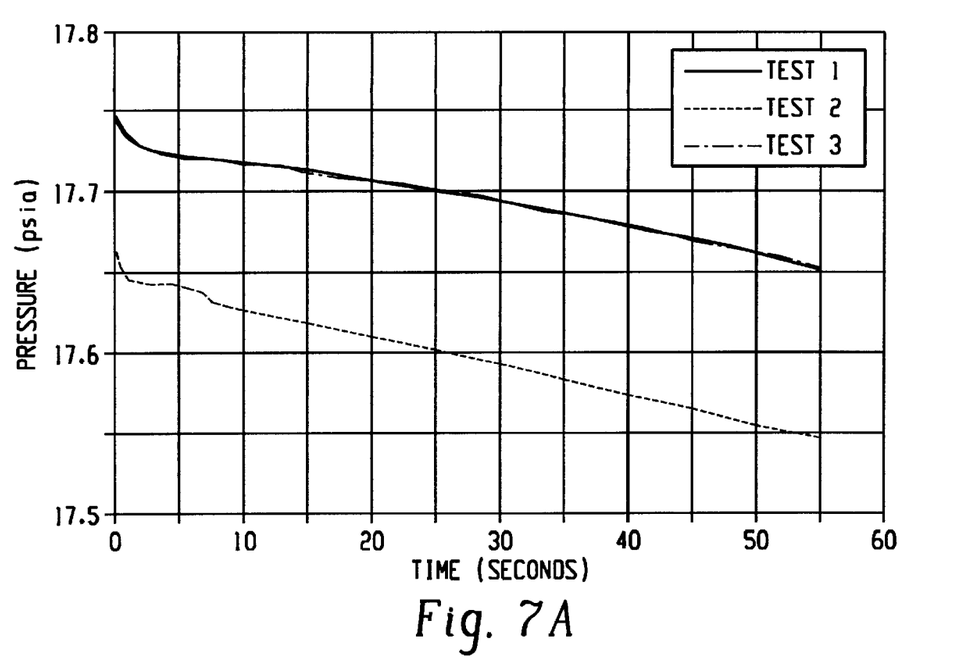
FIG. 7A is a plot of pressure vs time and FIG. 7B is a plot of change in volume vs time for an unsatisfactory endoscope.
Figure 7B:
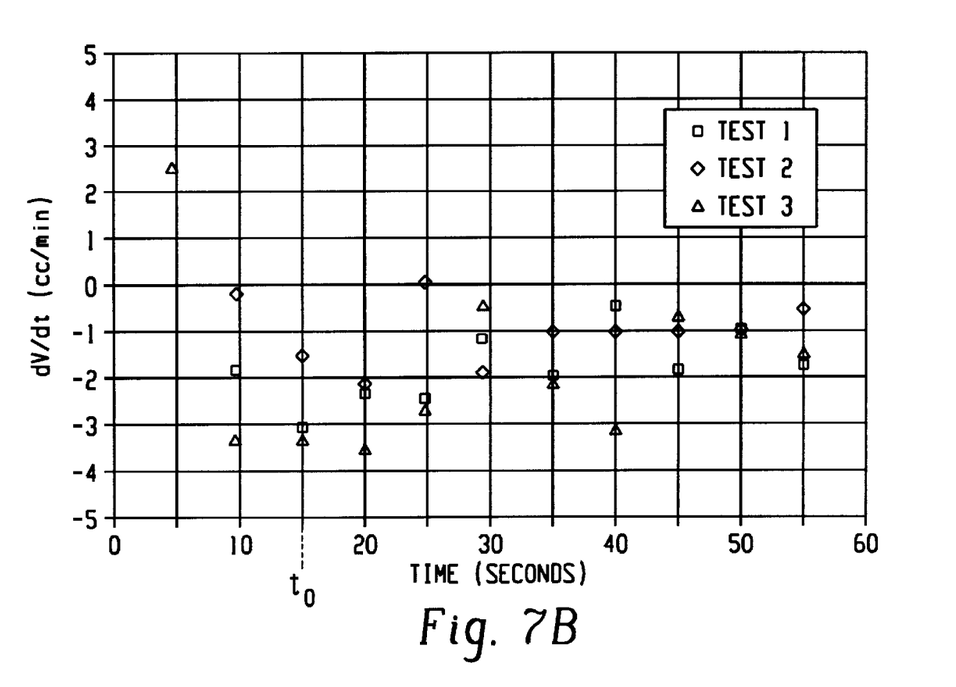

The endoscope represented in FIGS. 7A and 7B failed the test. As shown in FIG. 7A, the pressure continued to drop at a significant rate throughout the test. FIG. 7B shows that the rate of change of volume was, on average, in excess of 3 cc/minute. Additionally, the high rate of loss in volume continued throughout the test period, suggesting the endoscope was defective.

Figure 8:
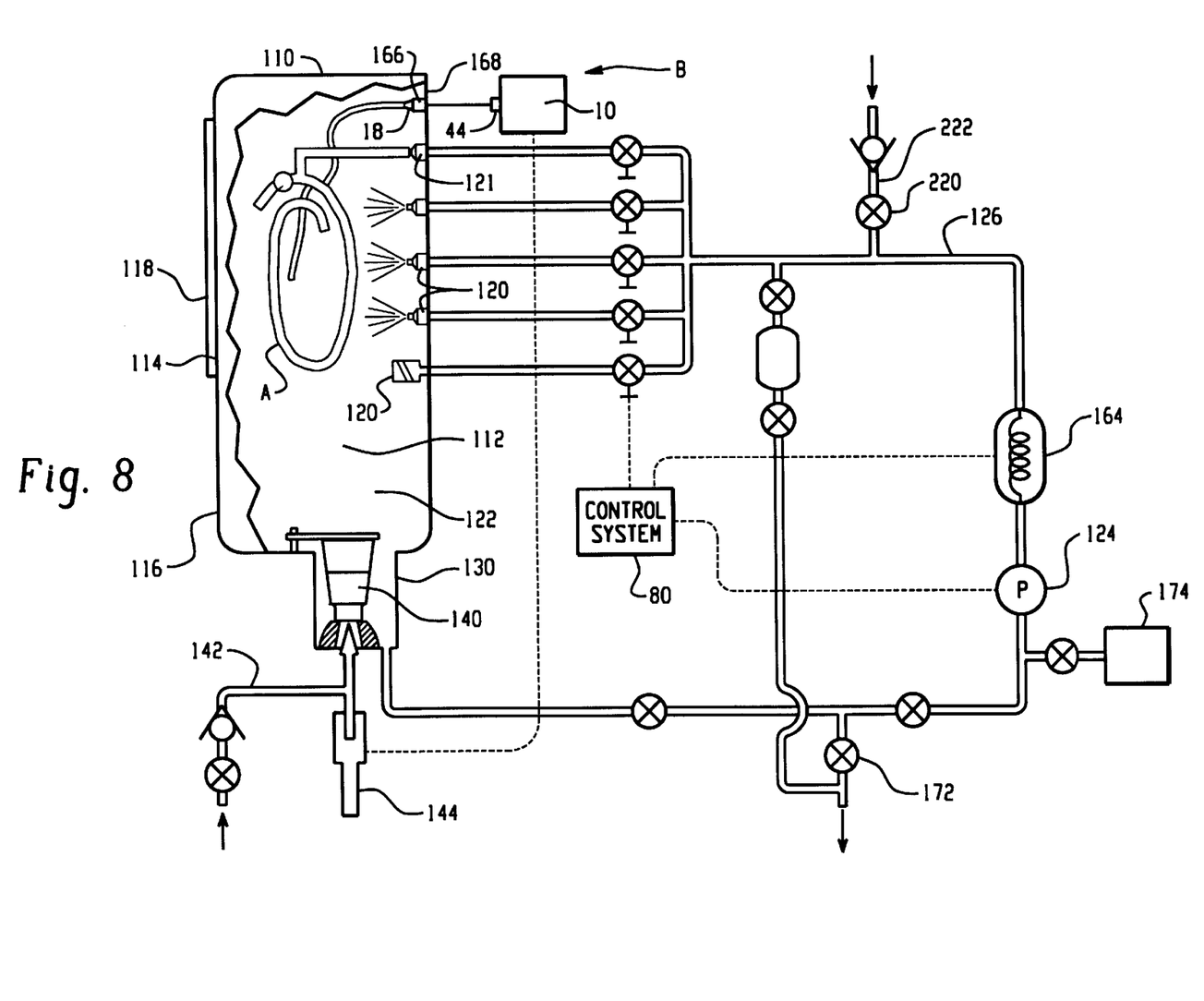
FIG. 8 is a plumbing diagram of an endoscope reprocessing unit incorporating the endoscope leak detector of FIG. 1.

The leak detector 10 can be used to detect for endoscope leaks prior to immersion of the endoscope A in a washing and/or disinfection fluid. Preferably, as shown in FIG. 8, the leak detector is incorporated into an automated washing and microbial decontamination processor B for reprocessing endoscopes.

While particular reference is made to the washing and microbial decontamination of endoscopes, it is to appreciated that the system may also be used to clean and decontaminate a variety of lumened instruments and other devices.

The processor B includes at least one combined washing and microbial decontamination cabinet 110 which defines an interior washing and microbial decontamination chamber 112. Items to be washed and microbially decontaminated are loaded into the chamber 112 through an opening 114 in a vertical front wall 116 of the cabinet closed by a door 118. Within the chamber, jets 120 spray a washing/decontaminant solution over the exterior surface of the endoscopes and other items and connection ports 121 direct the solution through internal passages of the endoscopes and other objects with lumens.

A collection tank or sump 122 forms the base of the cabinet 110 and receives the sprayed washing/decontaminant solution as it drops off the items. A high pressure pump 124 delivers the washing/decontaminate solution under pressure to the spray system through a fluid distribution system 126. A well or mixing chamber 130 sequentially receives doses of a cleaner concentrate and a concentrated decontaminant from separate compartments of a disposable cup 140. The concentrates mix with incoming tap water to form washing and antimicrobial decontamination solutions, respectively.

A preferred antimicrobial agent is peracetic acid, either in concentrated liquid form or as a reaction product of powdered reagents, such as acetyl salicylic acid and sodium perborate. However, it is also contemplated using other liquid or powdered decontaminants or reagents which react in a common solvent to generate peracetic acid, chlorine, hydrogen peroxide, hypochlorous acid, hypochlorite, or other strong oxidants which have biocidal effects. Aldehydes, such as glutaraldehyde, may be used, if care is taken with disposal.

A water inlet line 142 supplies water, typically from a municipal water system, to the well 130. A cup cutter 144, at the base of the well, sequentially opens the compartments. The water mixes with detergents, corrosion inhibitors, the concentrated antimicrobial agent, and other selected components in the cup to form wash, decontaminant, or other solutions. A heater 164 in the fluid supply 126 heats the decontaminant solution to a preferred temperature for effective decontamination.

The control system 80 preferably controls the operation of the processor B, including the pump 124, valves, the cup cutter 144, and the heater 164, in addition to the leak detector 10. A leak testing and reprocessing cycle thus proceeds automatically, from leak testing through final rinsing, without the need for intervention by an operator or transport of the device from one instrument to another.

The leak detector 10 is connected to the endoscope via a connection port 166 in a wall 168 of the chamber 112. The quick connect 18 is connected with the connection port 166, which in turn is connected with the inlet port 44 of the leak detector, housed outside the chamber.

In a typical decontamination cycle, items to be decontaminated are first inserted into the cabinet 110 through the opening 114. The endoscope A to be cleaned is mounted on a rack or other suitable support (not shown) and inserted into the chamber with other items to be cleaned and decontaminated. The fluid connection ports 121 of the chamber are fluidly connected with their respective endoscope inlet ports. The leak detector 10 is connected with the endoscope umbilical port 12, as previously described. A fresh cup 140 is inserted into the well 130 and the chamber closed.

From this point on, the operations of the processor B are automatically controlled by the control system 80. There is no need for an operator to contact the items until all of the steps are complete. A typical cycle includes five phases, namely, a leak testing phase, a washing phase, a microbial decontamination phase, a rinse phase, and a drying phase, which are carried out in sequence. It is contemplated, however, that one or more of these phases may be eliminated, for example, the cycle may proceed directly from the leak testing phase to the microbial decontamination phase without an intermediate washing phase. Or, additional phases may be added to the cycle as appropriate, such as additional rinsing phases.

In the first phase, the control system 80 signals the leak detector 10 to check the endoscope A for leaks. The leak detector goes through the process outlined above.

If all is satisfactory, the washing phase begins. In this phase the items are sprayed and flushed with the washing solution to remove soils, particularly protein, which inhibit access of the decontaminant during the decontamination phase. In the washing phase, the control system signals the opening member 144, to open the cleaner concentrate compartment of the cup 140. The cleaner concentrate mixes with the water to form the washing solution and is delivered by the pump 124 under pressure to the nozzles 120 and the endoscope connection ports 121. A drain valve 172 is then opened to flush the washing solution from the system.

In the decontamination phase, the control system 80 allows more water into the system and signals the heater 164 to heat the water. The microbial decontaminant is then released into the solution. At the end of the decontaminating phase, the valve 172 opens once more to flush the decontaminant solution from the processor to the drain. Finally a sterile rinse water is supplied to the system for rinsing the decontaminated items without risk of recontamination. A source of sterile 174 water supplies the water to the system on demand. Finally, in the drying stage, the control system signals a valve 220 in an air line 222 to open and supply microbe-free air to the system to dry the decontaminated items. The air line is connected with the manifold 126 so that the air flows through the nozzles and connection ports, drying the interior and exterior surfaces of the endoscopes and other items.

The dried items are removed from the decontamination chamber 112 for immediate reuse or transferred to sterile pouches and stored until needed.

While the system B has been described with reference to nozzles which spray the washing and decontaminant solutions over the device A, other ways of contacting the device with the solutions are also contemplated, such as immersion of the device therein.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A leak detection system for evaluating the integrity of a device with an internal passage, the system comprising:
   a tubular member which defines an interior chamber of known volume having ports;
   a connector adapted for releasably connecting a first of the ports of the interior chamber with the internal passage of the device;
   a source of a compressed gas fluidly connected with a second of the ports of the interior chamber which supplies the interior chamber and the internal passage with gas;
   a valve, which selectively seals the interior chamber and the internal passage from the source of compressed gas, such that the interior chamber and the internal passage define a closed pressure system that is dominated by the internal passage;
   a means for determining a volume of the compressed gas supplied to the interior chamber and the internal passage;
   a pressure sensor in communication with the interior chamber, which detects pressure within the internal passage by detecting pressure in the interior chamber; and
   a temperature sensor within the interior chamber, which detects temperature of the gas within the internal passage by detecting temperature in the interior chamber;
   a means for:
   (a) determining a volume of the internal passage from (1) the known volume of the interior chamber, (2) the determined volume of supplied gas, and (3) the measured pressure and temperature in the interior chamber, and
   (b) determining whether leakage from the internal passage has occurred based on (1) the determined volume of the internal passage and (2) at least two pressure and temperature measurements.

2. The system of claim 1, further including:
   a pressure regulator, which regulates the pressure of the gas entering the chamber from the source of compressed gas.

3. The system of claim 1, further including:
a second valve between the source of compressed gas and the first valve, which selectively vents gas from the chamber to the atmosphere and relieves back-pressure on the first valve.

4. The system of claim 3, wherein the first and second valves are solenoid valves.

5. The system of claim 4, wherein the control system controls opening and closing of the first and second valves.

6. The system of claim 1, wherein the source of compressed gas includes an air compressor.

7. The system of claim 1, wherein the source of compressed gas includes a reservoir.

8. A method for detecting the integrity of a device with an internal passage of unknown volume undergoing reprocessing in a reprocessing chamber, the device being one in which the internal passage undergoes a change in temperature during testing, the method comprising:
(a) supplying a quantity of gas under pressure to the internal passage of the device and to an interior chamber, the quantity being dependent on the time taken to fill the internal passage to a selected pressure;
(b) measuring the time taken to fill the internal passage to the selected pressure;
(c) determining the quantity of gas in the internal passage from the time taken to fill the internal passage to the selected pressure;
(d) sealing the interior chamber and the internal passage to fix the determined volume;
(e) measuring a temperature and a pressure of the gas within the internal passage at a first time;
(f) measuring the temperature and pressure of the gas within the internal passage at a second time; and
(g) determining from the determined quantity of gas and a change in the measured temperatures and a change in the measured pressures of the gas at the first and second times whether leakage of the gas from the internal passage has occurred.

9. The method of claim 8 wherein step (b) includes:
determining whether the pressure in the internal passage reaches a minimum preselected pressure, and if the internal passage does not reach the minimum pressure, examining the device for damage prior to commencing step (e).

10. The method of claim 8 further including one of:
in response to an indication that leakage has occurred at a rate which exceeds a preselected acceptable rate, examining the device for damage; and
in response to an indication that leakage of the gas from the internal passage is at a rate which does not exceed the preselected acceptable rate, subjecting the device to a liquid decontamination process.

11. The method of claim 10, further including, prior to subjecting the device to the liquid decontamination process:
venting the gas from the interior chamber and the internal passage.

12. The method of claim 10, wherein the preselected acceptable rate is about one cubic centimeter per minute.

13. A method for testing the integrity of an endoscope device with an internal passage undergoing reprocessing in a reprocessing chamber, the reprocessing causing changes in temperature of the endoscope during the testing, the method comprising:
(a) placing the endoscope in a reprocessing vessel and releasably connecting the endoscope to a leak detection system;
(b) supplying a quantity of gas under pressure through a tubing section adjacent the releasable connection to the internal passage of the endoscope;
(c) determining whether the pressure in the tubing section reaches a minimum preselected pressure, and if the tubing section does not reach the minimum pressure, examining the endoscope for damage;
(d) measuring the time taken to fill the internal passage to a selected pressure;
(e) determining the quantity of gas in the internal passage from the time taken to fill the internal passage to a selected pressure;
(f) comparing the measured fill time with a preselected maximum fill time;
(g) sealing the tubing section and the internal passage to define a closed volume;
(h) measuring a temperature and a pressure of the gas within the tubing section closely adjacent the releasable connection at a first time;
(i) measuring the temperature and pressure of gas within the tubing section at a second time; and
(j) determining from a change in the measured temperatures and a change in the measured pressures of the gas within the tubing section at the first and second times whether leakage of the gas from the endoscope internal passage has occurred.

14. A method of leak testing an endoscope of undetermined internal lumen volume comprising:
filling the endoscope lumen to a preselected above atmospheric pressure;
determining a volume of gas used to fill the endoscope lumen to the preselected above atmospheric pressure;
a measured time interval after filling the endoscope lumen, determining a volume of gas remaining in the endoscope lumen;
from the determined fill volume, the determined remaining volume, and the measured time interval, determining a rate of change of the volume of gas in the endoscope lumen;
from the rate of volume change, determining whether unacceptable leakage has occurred.

15. The method as set forth in claim 14 wherein determining the fill volume includes:
measuring a fill time;
measuring a temperature of the gas when the interior endoscope volume is filled to the preselected above atmospheric pressure.

16. A method of detecting leaks in an endoscope having at least one lumen of unspecified volume, the method comprising:
filling the endoscope lumen with test gas;
determining a volume of the lumen from a quantity and pressure of the test gas used to fill the lumen;
measuring a drop in pressure over time of the test gas in the lumen;
from both the determined lumen volume and the pressure drop, determining whether leakage above a preselected level has occurred, such that dynamic compensation is made for the lumen volume.

* * * * *